US011950593B2

(12) United States Patent
Schlenoff et al.

(10) Patent No.: US 11,950,593 B2
(45) Date of Patent: Apr. 9, 2024

(54) ANTIMICROBIAL THIOURONIUM COPOLYMERS AND METHODS OF MAKING AND USING THE SAME

(71) Applicant: FLORIDA STATE UNIVERSITY RESEARCH FOUNDATION, INCORPORATED, Tallahassee, FL (US)

(72) Inventors: Joseph Schlenoff, Tallahassee, FL (US); Sandrine Lteif, Tallahassee, FL (US)

(73) Assignee: FLORIDA STATE UNIVERSITY RESEARCH FOUNDATION, INCORPORATED, Tallahassee, FL (US)

( * ) Notice: Subject to any disclaimer, the term of this patent is extended or adjusted under 35 U.S.C. 154(b) by 202 days.

(21) Appl. No.: 17/499,242

(22) Filed: Oct. 12, 2021

(65) Prior Publication Data

US 2022/0110320 A1 Apr. 14, 2022

Related U.S. Application Data

(60) Provisional application No. 63/090,854, filed on Oct. 13, 2020.

(51) Int. Cl.
| *A01N 33/12* | (2006.01) |
| *A01P 1/00* | (2006.01) |
| *A61L 2/18* | (2006.01) |
| *A61L 101/48* | (2006.01) |
| *C08F 220/60* | (2006.01) |

(52) U.S. Cl.
CPC ............... *A01N 33/12* (2013.01); *A01P 1/00* (2021.08); *A61L 2/18* (2013.01); *C08F 220/60* (2013.01); *A61L 2101/48* (2020.08); *C08F 2800/10* (2013.01)

(58) Field of Classification Search
CPC ...... C08F 220/60; C08F 2800/10; A61L 2/18; A61L 2101/48; A01N 33/12; A01P 1/00
See application file for complete search history.

(56) References Cited

PUBLICATIONS

Ltief et al., "The Thiouronium Group for Ultrastrong Pairing Interactions between Polyelectrolytes" in The Journal of Physical Chemistry 2020, 124, pp. 10832-10840. (Year: 2020).*
Cohen et al., "Engineering of crosslinked polyisothiouronium methylstyrene microparticles of narrow size distribution for antibacterial applications" in Polym. Adv. Technol. 2017, 28, pp. 1730-1734, a Research article. (Year: 2017).*
Schlenoff et al., "Adsorption of Thiol-Containing Copolymers onto Gold" in Macromolecules 1995, 28, pp. 4290-4295. (Year: 1995).*

* cited by examiner

*Primary Examiner* — Blessing M Fubara
(74) *Attorney, Agent, or Firm* — Thomas | Horstemeyer, LLP

(57) ABSTRACT

Described herein are antimicrobial copolymers comprising (i) a polymer backbone and a plurality of thiouronium groups covalently bonded to the polymer backbone and (ii) a plurality of quaternary ammonium groups covalently bonded to the polymer backbone. Also described herein are methods for making the copolymers described herein and their use in disinfecting compositions.

17 Claims, 4 Drawing Sheets

ANTIMICROBIAL THIOURONIUM COPOLYMERS AND METHODS OF MAKING AND USING THE SAME

CROSS-REFERENCE TO RELATED APPLICATIONS

This application claims the benefit of and priority to co-pending U.S. Provisional Patent Application No. 63/090,854, filed on Oct. 13, 2020, the contents of which are incorporated by reference herein in its entirety.

BACKGROUND

Pathogenic microbes include viruses, bacteria and fungi as well as some single-celled organisms such as amoebae. Chemical agents are needed to kill these pathogens. Generally known as disinfectants, there are a number of commercially available chemicals useful for killing pathogenic microbes, such as alcohol, bleach, quaternary ammonium compounds, soap and hydrogen peroxide. These are applied externally to surfaces on which microbes may attach or proliferate. A limited selection of broad-spectrum antimicrobials is approved for limited in-vivo use, such as cetylpyridinium chloride in mouthwash.

For effective contact-killing of microbes, disinfectants need to remain in contact with microbes for a minimal time, even a few seconds. Molecules with low vapor pressure, such as soaps or surfactants, remain on surfaces longer, whereas ethanol or isopropanol evaporate relatively quickly. In addition, small molecules are easily wiped off smooth surfaces, limiting the time that surface may be considered microbe-free.

The mechanism of antimicrobial activity varies according to the disinfectant used. Surfactants are thought to kill microbes directly by disrupting their cell membranes. Well-suited for this purpose are cationic surfactants, such as quaternary ammonium salts which include the well-known disinfectant Lysol. The mechanism of cell membrane disruption is thought to be aided by the interaction of the positive charge on the surfactant with negative charges on the cell membrane.

There is a need for an effective disinfectant that can be applied to a surface, alone or in conjunction with other disinfectants that also remains on said surface and is resistant to removal by wiping or washing.

SUMMARY

Described herein are antimicrobial copolymers comprising (i) a polymer backbone and a plurality of thiouronium groups covalently bonded to the polymer backbone and (ii) a plurality of quaternary ammonium groups covalently bonded to the polymer backbone. In one aspect, the thiouronium group comprises the structure

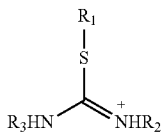

wherein $R_1$ is an aryl group, an alkylene group, or an aralkyl group that is covalently bonded to the polymer backbone, and $R_2$ and $R_3$ are independently hydrogen, an alkyl group, or an aryl group. In another aspect, the quaternary ammonium group has the structure

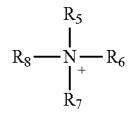

wherein $R_5$ is an aryl group or an alkylene group and is covalently bonded to the polymer backbone, and $R_6$, $R_7$ and $R_8$ are an alkyl group or an aryl group.

Also described herein are methods for making the copolymers described herein and their use in disinfecting compositions.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figures 1A, 1B:
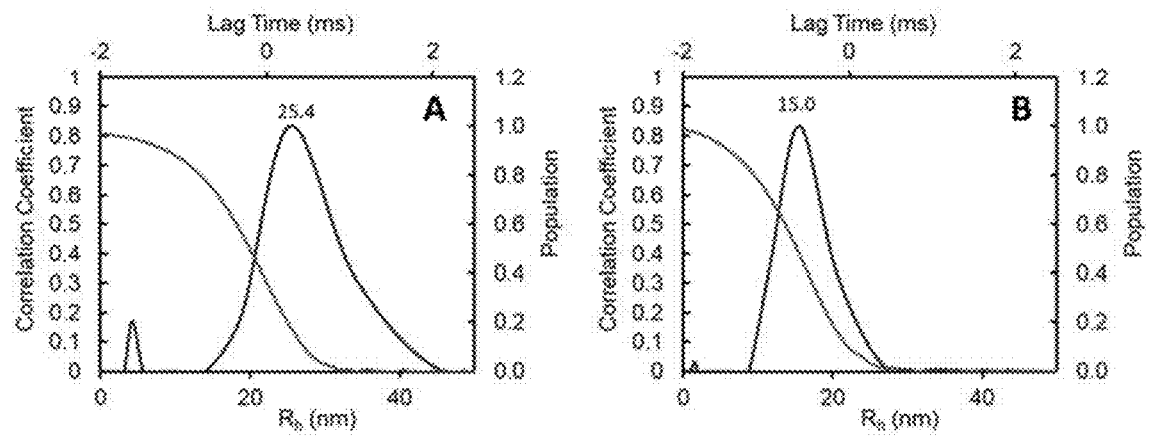
FIGS. 1A-1B show the autocorrelation function and hydrodynamic radius, $R_h$, distribution of PVBT in 0.1M TEABr at an angle of 30°, 1 mg/mL concentration at (A) 296.8K and (B) 339.8K.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a solvent" include, but are not limited to, mixtures or combinations of two or more such solvents, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein. In one aspect, the heterocycloalkyl group can be a lactam, including but not limited to an N-substituted lactam.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl. Fused aryl groups including, but not limited to, indene and naphthalene groups are also contemplated.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "alkylene" as used herein is represented by the formula —$(CR_2)_n$-, where n is an integer from 1 to 10 and each R is hydrogen or an alky group as defined herein. Examples of alkylene groups include methylene, ethylene, or propylene.

The term "aralkyl" as used herein is an aryl group as defined herein where one or more atoms of the aryl group is substituted with an alkylene group as defined herein. An example of an aralkyl group is a benzyl group ($C_6H_5$—$CH_2$—)

The term "halide," as used herein can be used interchangeably and refer to $F^-$, $Cl^-$, $Br^-$, or $I^-$.

The term "alkoxide" as used herein is represented by the formula $RO^-$, where R is an alkyl group, cycloalkyl group, or aryl group as defined above.

The term "carboxylate" as used herein is represented by the formula $RC(O)O^-$, where R is an alkyl group, cycloalkyl group, or aryl group as defined above.

A "residue" refers to a fragment, group, or substructure of a molecule described herein, regardless of how the molecule is prepared. For example, a thiouronium group can have the structure:

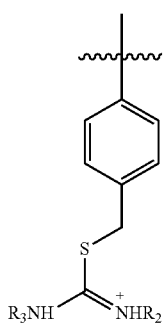

where the structure is a residue or component of the copolymers described herein.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to conduct the methods of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

Described herein are antimicrobial copolymers comprising (i) a polymer backbone and a plurality of thiouronium groups covalently bonded to the polymer backbone and (ii) a plurality of quaternary ammonium groups covalently bonded to the polymer backbone. Also described herein are methods for making the copolymers described herein and their use in disinfecting compositions.

Copolymers

The copolymers described herein can also be referred to as a "polyelectrolyte" that comprises multiple electrolytic repeat units that dissociate in solution, which makes the copolymer charged. The polyelectrolytes described herein, depending on the chemical nature of the thiouronium group and the presence of suitable comonomers, may be soluble in water or in organic solvent or in a mixture of water and organic solvent.

The copolymers described herein comprise a plurality of thiouronium groups covalently bonded to a polymer backbone. A thiouronium group is a cationic form of a thiourea group or a derivatized thiourea group. In one aspect, the thiouronium group has the structure I

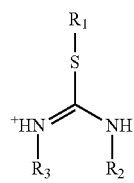

I wherein $R_1$ is an aryl group, an alkylene group, or an aralkyl group that is covalently bonded to the polymer backbone, and $R_2$ and $R_3$ are independently hydrogen, an alkyl group, or an aryl group.

In one aspect, $R_1$ is $C_1$ to $C_8$ alkylene group. In another aspect, $R_1$ is a substituted or unsubstituted benzyl group. In another aspect, $R_2$ and $R_3$ are, independently, $—C_nH_{2n+1}$ where n is 1-18, or 1-8.

In one aspect, the thiouronium group comprises the structure II

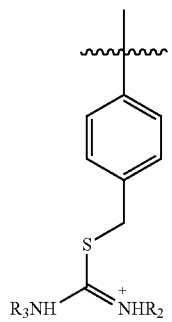

II where $R_2$ and $R_3$ are defined above. In one aspect, $R_2$ and $R_3$ in structure II are each a $C_2$ to $C_6$ alkyl group.

In one aspect, an exemplary structure of the copolymer comprising a thiouronium group is provided in structure III

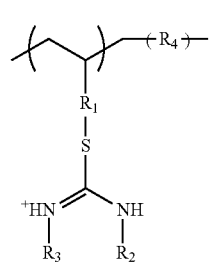

III where $R_1$, $R_2$, and $R_3$ as defined above is covalently bonded to the polymer backbone.

Referring to structure III, $R_4$ can be derived from a variety of different monomers. In one aspect, in addition to thiouronium groups, the copolymers described herein can include additional positively charged repeat units. These additional positive charged repeat units are themselves preferably water soluble and assist in bringing the thiouronium to the surface of the cell membrane by interacting with negative charges on the cell membrane.

The copolymers described herein include a plurality of quaternary ammonium groups covalently bonded to the polymer backbone. The term "quaternary ammonium group" is a group bearing a permanently positively charged nitrogen atom, as opposed to an amine, which may be protonated.

In one aspect, the quaternary ammonium group has the structure IV

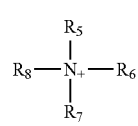

IV wherein $R_5$ is an aryl group or an alkylene group and is covalently bonded to the polymer backbone, and $R_6$, $R_7$ and $R_8$ are independently an alkyl group or an aryl group. In one aspect, $R_6$, $R_7$ and $R_8$ are each a $C_1$ to $C_5$ alkyl group. In another aspect, $R_6$, $R_7$ and $R_8$ are each a methyl group.

In one aspect, the quaternary ammonium group has the structure V

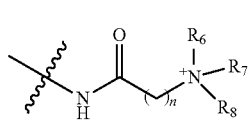

V wherein n is an integer from 1 to 6, and $R_6$, $R_7$ and $R_8$ are independently an alkyl group, or an aryl group. In one aspect, n is 3.

In one aspect, the quaternary ammonium group comprises a nitrogen-bearing heteroaryl group, wherein nitrogen is alkylated. For example, the heteroaryl group can be a pyridinium group such as a N-methylvinylpyridinium (MVP). In another aspect, the quaternary ammonium group comprises a nitrogen-bearing cycloalkyl group, wherein nitrogen is alkylated. Non-limiting examples of these groups are provided in Table 1.

TABLE 1

| Name | Structure |
|---|---|
| diallyldimethylammonium (PDADMA) | (structure shown) |
| N-methyl-2-vinyl pyridinium (PM2VP) | (structure shown) |
| N-methyl-4-vinyl-pyridinium (PM4VP) | (structure shown) |
| N-octyl-4-vinylpyridinium (PNO4VP) | (structure shown) |
| N-methyl-2-vinyl pyridinium-co-ethyleneoxide (PM2VP-co-PEO) | (structure shown) |

X and Y denote proportions of repeat units

TABLE 2

| Name | Structure |
|---|---|
| Acrylamide | (structure shown) |
| Vinylpyrrolidone | (structure shown) |
| Ethylene oxide | (structure shown) |
| Vinylcaprolactam | (structure shown) |

In one aspect, the copolymers described herein can include an uncharged repeat unit that is not pH sensitive in the operating pH range, for example, about pH 3 to about pH 9. In one aspect, the uncharged repeat unit is hydrophilic. Uncharged hydrophilic repeat units useful herein include, but are not limited to, acrylamide, vinyl pyrrolidone, ethylene oxide, and vinyl caprolactam. Non-limiting examples of uncharged repeat units are shown in Table 2. In other aspects, uncharged repeat units also include N-isopropylacrylamide and propylene oxide.

In one aspect, the copolymers include zwitterionic groups or repeat units. For example, the zwitterionic group can include an quaternary ammonium group and a sulfate group. Such an example is PAEDAPS provided in Scheme 3 in the Examples. Though zwitterionic repeat units contribute equal number of positive and negative repeat units, the zwitterionic group is still solvated and relatively hydrophilic.

In one aspect, the copolymers described herein do not include repeat units that are net negatively charged in solutions of the copolymer. Not wishing to be bound by theory, these negatively charged units interact with the thiouronium units and thus render the copolymer insoluble. In one aspect, the copolymers described herein have a net positive charge.

Preparation of the Copolymers

The copolymers described herein can be produced by a number of different synthetic techniques depending upon the nature of the copolymer. In one aspect, the copolymer is a synthetic polymer. In one aspect, the copolymer can be produced by polymerizing monomers having a thiouronium group with other monomers having cationic groups, (e.g., quaternary ammonium groups), neutral groups, or zwitterionic groups. In one aspect, the copolymer comprises the polymerization product between a first olefinic monomer having a thiouronium group and a second olefinic monomer having a quaternary ammonium group. In one aspect, the monomers have the structures VI and VII

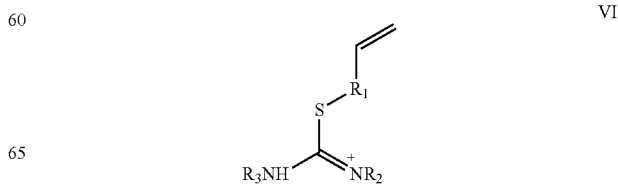

VI

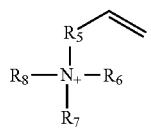

(VII)

where $R_1$ to $R_8$ are as defined above. The Examples provide non-limiting procedures for making synthetic copolymers by the polymerization of olefinic monomers.

In another aspect, a polymer can be modified by chemical reactions to covalently attach a plurality of thiouronium groups to the polymer.

In another aspect, naturally occurring biomacromolecules can be chemically modified to attach thiouronium groups to the biomacromolecule. Examples of biomacromolecules that may be modified with thiouronium functional groups for use herein include proteins, polypeptides, enzymes, chitosan, chitosan sulfate, cellulose sulfate, polysaccharides, carrageenin, hyaluronic acid, and carboxymethylcellulose. Positively-charged biomacromolecules can include protonated sub-units (e.g., protonated amines). If a biomacromolecule includes a negative charge such as a carboxylate, the negative charge can be converted into a neutral group or a positive charge. Depending upon the biomacromolecule, the copolymer may be degraded or consumed by natural organisms ("biodegradable").

The copolymers described herein are generally positively charged species when dissolved in a solvent. In one aspect, the copolymers in dry form are a salt composed of the copolymer and a counterion. When the copolymer salt is added to a solvent, the counterions dissociate in water. The counterion is any suitable anion such as, for example, a halide, sulfate or a carboxylate. The positive charge of the copolymers described herein can be produced by a number of different synthetic techniques. In one aspect, a copolymer having a plurality of thiourea groups can be added to a solvent and subsequently protonated or alkylated to produce thiouronium groups in situ. For example, a copolymer composed of thiourea groups can be protonated with HCl to produce thiouronium groups with Cl⁻ as the counterion. In another aspect, monomers having thiouronium groups can be polymerized with other monomers as discussed above.

In one aspect, the copolymers described herein can be branched. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. In one aspect, the branched copolymers comprising thiouronium groups can be star polymers, comb polymers, graft polymers, and dendritic polymers.

In one aspect, the copolymers can be block copolymers. For example, the block copolymer can include a block of thiouronium groups and a block of quaternary ammonium groups. The number of blocks can vary. In one aspect, the number of different blocks in the copolymer can be from 2 to 5, or 2 or 3. In one aspect, when the number of blocks is 3, the block arrangement is ABA.

The molecular weight (number average) of the copolymers can vary. In one aspect, the copolymers have a molecular weight of about 1,000 grams/mole to about 5,000,000 grams/mole, or about 10,000 grams/mole to about 1,000,000 grams/mole, or 10,000 grams/mole, 50,000 grams/mole, 100,000 grams/mole, 150,000 grams/mole, 200,000 grams/mole, 250,000 grams/mole, 300,000 grams/mole, 350,000 grams/mole, 400,000 grams/mole, 450,000 grams/mole, 500,000 grams/mole, 550,000 grams/mole, 600,000 grams/mole, 650,000 grams/mole, 700,000 grams/mole, 750,000 grams/mole, 800,000 grams/mole, 850,000 grams/mole, 900,000 grams/mole, 950,000 grams/mole, or 1,000,000 grams/mole, where any value can be a lower or upper endpoint of a range (e.g., 450,000 grams/mole to 800,000 grams/mole). In another aspect, when the copolymer is a naturally occurring polymer, the molecular weight can be up to 10,000,000 grams/mole.

The amount of thiouronium groups present in the copolymers described herein can vary depending upon the application of the copolymers. In one aspect, the amount of the thiouronium groups can be modified by varying the amount of the monomer bearing the thiouronium group relative to other monomers used to produce the copolymer. In one aspect, the molar ratio of thiouronium groups to quaternary ammonium groups in the copolymer is from 1:20 to 20:1, or 1:20, 1:18, 1:16, 1:12, 1:10, 1:8, 1:6, 1:4, 1:2, 1:1, 2:1, 4:1, 6:1, 8:1, 10:1, 12:1, 14:1, 16:1, 18:1, or 20:1, where any value can be a lower or upper endpoint of a range (e.g., 2:1 to 1:4).

Disinfection Compositions and Applications Thereof

The copolymers described herein can be formulated as compositions for disinfecting substrates and surfaces. The compositions are composed of the copolymer and a solvent. An appropriate solvent is one in which the selected copolymer is soluble. Thus, the appropriate solvent depends on whether the copolymer is considered to be hydrophobic or hydrophilic. A hydrophobic polymer displays a less favorable interaction energy with water than a hydrophilic polymer. While a hydrophilic polymer is water soluble, a hydrophobic polymer may only be sparingly soluble in water, or, more likely, insoluble in water. Likewise, a hydrophobic polymer is more likely to be soluble in organic solvents than a hydrophilic polymer. In general, the higher the carbon to charge ratio of the polymer, the more hydrophobic it tends to be. For example, polyvinyl pyridine alkylated with a methyl group (PNMVP) is considered to be hydrophilic, whereas polyvinyl pyridine alkylated with an octyl group (PNOVP) is considered to be hydrophobic. In one aspect, water is used as the solvent for hydrophilic copolymers and organic solvents such as an alcohol (e.g., ethanol, isopropanol) is used for hydrophobic copolymers.

In one aspect, the solvent comprises at least 50 weight percent ethanol, isopropanol, or a combination thereof. In another aspect, the solvent is 50 weight percent, 55 weight percent, 60 weight percent, 65 weight percent, 70 weight percent, 75 weight percent, 80 weight percent, 85 weight percent, 90 weight percent, 95 weight percent, or 100 weight percent ethanol, isopropanol, or a combination thereof, where any value can be a lower or upper endpoint of a range (e.g., 60 weight percent to 85 weight percent).

The concentration of the copolymer present in the disinfecting composition can vary depending upon the application. In one aspect, the copolymer is from about 0.001 weight percent to about 1.0 weight percent of the disinfecting composition, or about 0.001 weight percent, 0.005 weight percent, 0.01 weight percent, 0.05 weight percent, 0.1 weight percent, 0.2 weight percent, 0.3 weight percent, 0.4 weight percent, 0.5 weight percent, 0.6 weight percent, 0.7 weight percent, 0.8 weight percent, 0.9 weight percent, or 1.0 weight percent, where any value can be a lower or upper endpoint of a range (e.g., 0.01 weight percent to 0.1 weight percent).

A surface contacted with a copolymer described herein retains antimicrobial properties for a period of time due to the fact that the copolymer adheres to the surface of the substrate and will not evaporate. In one aspect, the copolymer described herein may be dispersed in a solvent and used directly for disinfecting, or the copolymer can be dispersed in a solvent, wiped on a clean surface, whereupon said surface, now treated with the copolymer, possesses extended resistance over time against contamination by organisms such as, for examples, bacterial, viruses, fungi, and other harmful pathogens.

In one aspect, described herein are methods for disinfecting a substrate comprising applying to the substrate a disinfecting composition comprising a copolymer described herein. In one aspect, the disinfecting compositions described herein can prevent the growth of an organism on a substrate. In another aspect, the disinfecting compositions described herein can reduce the rate of growth of organism on a substrate. In another aspect, the disinfecting compositions described herein can kill or eliminate the majority or all of the organisms present on a substrate. The substrate can be any surface or material, or article where it is desirable to reduce or prevent the growth of harmful organism.

The disinfecting composition can be applied to a substrate by a variety of techniques. In one aspect, for fast throughput and coating of surfaces, the disinfecting composition can be applied to a surface of the substrate by spraying, coating, or dipping. Spraying is especially preferred when applying the coating to large areas. The disinfecting compositions may be sprayed onto a substrate by any applicable means (e.g., an atomizer, an aspirator, ultrasonic vapor generator, entrainment in compressed gas, or inkjet sprayer). In one aspect, a hand operated sprayer can be used to spray the disinfecting composition. In one aspect, the droplet size in the spray is about 10 nm to about 1 mm in diameter, or about 10 μm to 100 μm in diameter. In another aspect, the coverage of the spray is typically about 0.001 mL/cm$^2$ to 1 mL/cm$^2$.

Not wishing to be bound by theory, the thiouronium groups present in the copolymers described herein maximize the interaction of the copolymer with negative charges external to the copolymer, such as negative charges on the surface of a pathogen. The Examples demonstrate the strength of interactions between thiouronium groups and negative charges is very high, which makes the copolymers in the disinfecting composition described herein useful in binding and killing organisms that possess a negative surface charge.

The external surface of cell membranes, including viral and bacterial membranes, comprises phospholipids. These phospholipids are uncharged, negatively charged, or zwitterions (such as phosphatidylcholine). For maximum efficiency at disrupting/destroying cell membranes it is preferred that disinfectants interact strongly with zwitterionic groups. As demonstrated in the Examples, copolymers described herein interact strongly with a zwitterionic polymer, whereas copolymers that do not possess thiouronium groups interact more weakly with zwitterionic polymers. Thus, the copolymers and disinfecting compositions described herein are particularly effective at interacting with zwitterionic lipids, which makes them effective at destroying lipid membranes of pathogens.

Aspects

Aspect 1. An antimicrobial copolymer comprising (i) a polymer backbone and a plurality of thiouronium groups covalently bonded to the polymer backbone and (ii) a plurality of quaternary ammonium groups covalently bonded to the polymer backbone.

Aspect 2. The copolymer of Aspect 1, wherein the thiouronium group comprises the structure

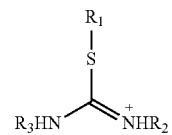

wherein $R_1$ is an aryl group, an alkylene group, or an aralkyl group that is covalently bonded to the polymer backbone, and $R_2$ and $R_3$ are independently hydrogen, an alkyl group, or an aryl group.

Aspect 3. The copolymer of Aspect 2, wherein $R_1$ is $C_1$ to $C_8$ alkylene group.

Aspect 4. The copolymer of Aspect 2, wherein $R_1$ is a substituted or unsubstituted benzyl group.

Aspect 5. The copolymer of Aspect 2, wherein the thiouronium group comprises the structure

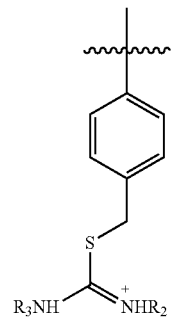

Aspect 6. The copolymer of Aspect 2, wherein $R_2$ and $R_3$ are each a $C_2$ to $C_6$ alkyl group.

Aspect 7. The copolymer of Aspect 1, wherein the quaternary ammonium group comprises a nitrogen-bearing heteroaryl group, wherein nitrogen alkylated.

Aspect 8. The copolymer of Aspect 1, wherein the quaternary ammonium group comprises a nitrogen-bearing cycloalkyl group, wherein nitrogen is alkylated.

Aspect 9. The copolymer of Aspect 1, wherein the quaternary ammonium group has the structure

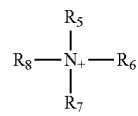

wherein $R_5$ is an aryl group or an alkylene group and is covalently bonded to the polymer backbone, and $R_6$, $R_7$ and $R_8$ are independently an alkyl group or an aryl group.

Aspect 10. The copolymer of Aspect 9, wherein the quaternary ammonium group has the structure

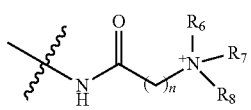

wherein n is an integer from 1 to 6.

Aspect 11. The copolymer of Aspect 10, wherein n is 3.

Aspect 12. The copolymer of any one of Aspects 9-11, wherein $R_6$, $R_7$ and $R_8$ are each a $C_1$ to $C_5$ alkyl group.

Aspect 13. The copolymer of any one of Aspects 9-11, wherein $R_6$, $R_7$ and $R_8$ are each a methyl group.

Aspect 14. The copolymer of any one of Aspects 1-13, wherein the copolymer comprises a plurality of zwitterionic groups covalently bonded to the polymer backbone.

Aspect 15. The copolymer of any one of Aspects 1-13, wherein the polymer backbone comprises a naturally occurring biomacromolecule or a synthetic polymer.

Aspect 16. The copolymer of Aspect 1, wherein the copolymer comprises the polymerization product between a first olefinic monomer having a thiouronium group and a second olefinic monomer having a quaternary ammonium group.

Aspect 17. The copolymer of any one of Aspects 1-16, wherein the copolymer has an average molecular weight of from about 1,000 grams/mole to about 5,000,000 grams/mole.

Aspect 18. The copolymer of any one of Aspects 1-17, wherein the molar ratio of thiouronium groups to quaternary ammonium groups in the copolymer is from 1:20 to 20:1.

Aspect 19. The copolymer of any one of Aspects 1-18, wherein the copolymer further comprises a counterion Aspect 20. The copolymer of Aspect 19, wherein the copolymer further comprises a counterion comprising a halide, sulfate or a carboxylate.

Aspect 21. A composition for disinfecting a substrate comprising the copolymer of any one of Aspects 1-20.

Aspect 22. The composition of Aspect 21, wherein the copolymer is from about 0.001 weight percent to about 0.1 weight percent of the composition.

Aspect 23. The composition of Aspect 21 or 22, wherein the composition comprises a solvent comprising water, an alcohol, or a combination thereof.

Aspect 24. The composition of Aspect 23, wherein the alcohol comprises ethanol, isopropanol, or a combination thereof.

Aspect 25. The composition of Aspect 23 or 24, wherein the solvent comprises at least 50 weight percent ethanol, isopropanol, or a combination thereof.

Aspect 26. A method for disinfecting a substrate comprising applying to the substrate the composition of any one of Aspects 21-25.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure.

Materials and Techniques. 4-Vinylbenzylchloride (VBCl) was from Scientific Polymer Products. Thiourea, acryloyl chloride, [3-(methacryloylamino)propyl]trimethylammonium chloride solution (MAPTAC) in 50 wt % water, acetone, 2,2,2-trifluoroethanol (TFE), ammonium persulfate and tetraethylammonium bromide (TEABr) were obtained from Sigma Aldrich. N,N'-dimethylethylenediamine and 1,3-propane sulfone were from Alfa Aesar. Diethyl ether, ethanol (EtOH) methanol (MeOH) and dimethylsulfoxide (DMSO) were from VWR chemicals. Initiators 2,2'-azobis (2-methylbutyronitrile) (VAZO-67) and 2,2'-azobis[N-(2-carboxyethyl)-2-methylpropionamidine] hydrate (VA-057) were from Miller-Stephenson Chemical Co and Wako respectively. Sodium acetate (NaAc) was from Fisher Scientific and deuterium oxide ($D_2O$) from Cambridge Isotope Laboratories. Deionized water (18.2 MΩ cm, Milli-Q) was used to prepare all aqueous solutions.

Synthesis of VBT. The positively charged monomer VBT was synthesized from VBCl and thiourea: to a solution of VBCl (3.05 g, 20 mmol) in 22.9 mL ethanol and 22.9 mL acetone, thiourea (1.38 g, 18 mmol) was added and the mixture stirred for 18 h under reflux at 65° C. After precipitation of the concentrated reaction mixture into diethyl ether, the crude product was recrystallized using a 1:4 ratio of methanol to diethyl ether to yield VBT (60% yield). $^1$H NMR (600 MHz, $D_2O$) δ 7.43 (d, J=7.9 Hz, 2H), 7.35 (d, J=8.0 Hz, 2H), 6.70 (dd, J=17.7, 10.9 Hz, 1H), 5.81-5.75 (m, 1H), 5.26 (d, J=10.9 Hz, 1H), 4.31 (s, 2H).

Scheme 1. Synthesis of the cation monomer and polycation PVBT

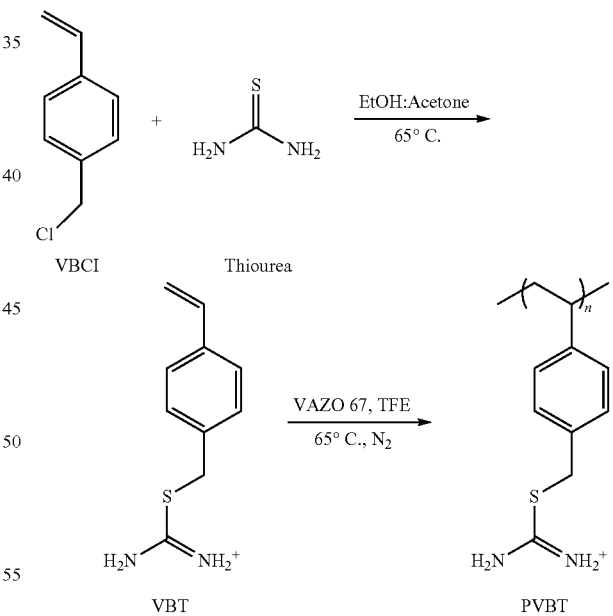

Synthesis of PVBT polyelectrolyte. VAZO-67 8.4 mg (1%) was added to 4.4 mmol PVBT in 20 ml TFE. The mixture was left to stir at 65° C. for 24 h under $N_2$. The crude polymer was precipitated using diethyl ether and purified by dialysis against water (SnakeSkin, molecular weight cutoff, MWCO=3500) at 4° C. for 48 h. The PVBT homopolymer was isolated after freeze-drying (yield 81%). $^1$H NMR (600 MHz, $D_2O$, Figure S1) δ 7.09 (s, 4H), 4.29 (s, 2H), 2.50-0.28 (s, 3H).

Scheme 2. Synthesis scheme of PMAPTAC$_{0.91}$-co-PVBT$_{0.09}$

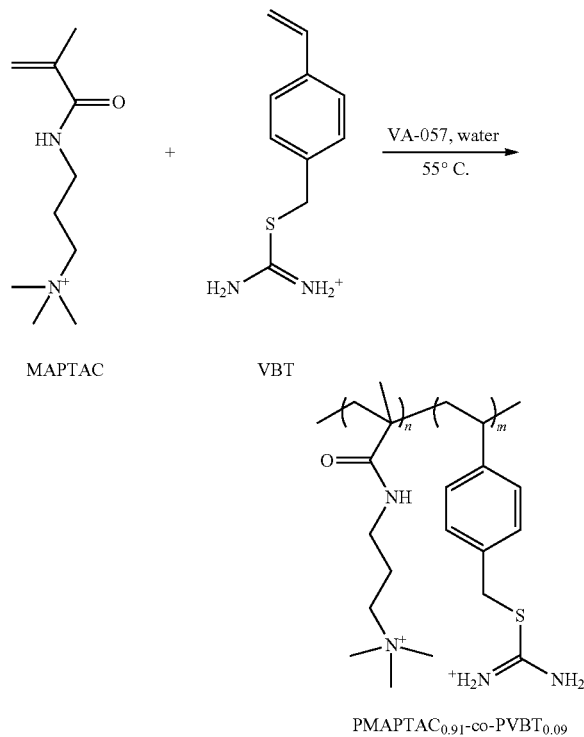

PMAPTAC-co-PVBT copolymer. MAPTAC (4.5 mmol) and VBT monomer (0.115 g, 0.5 mmol) were mixed with 21 mg (1%) VA-057 in 10 mL water and stirred at 55° C. under $N_2$. The copolymer was purified by dialyzing against water for 48 h and recovered by evaporating the water at 70° C. under reduced pressure (60% yield). The composition was found to be PMAPTAC$_{0.91}$-co-PVBT$_{0.09}$ by $^1$H NMR (600 MHz, $D_2O$, Figure S2) δ 7.09 (d, J=145.6 Hz, 4H), 4.32 (s, 2H), 3.32 (t, J=8.0 Hz, 15H), 3.10 (s, 97H), 2.30 (s, 4H), 1.97 (s, 19H), 1.68 (s, 13H), 0.97 (d, J=84.2 Hz, 23H).

Synthesis of PMAPTAC and PMA PMAPTAC and PMA were synthesized following an aqueous radical polymerization procedure. PMA was neutralized using sodium hydroxide to pH 9 before being precipitated and dried under vac at 65° C.

Synthesis of AEDA, AEDAPS and PAEDAPS. Zwitterion monomers AEDA and AEDAPS were synthesized following literature procedures, where a coupling reaction between N, N-dimethylethylenediamine and acryloyl chloride and AEDA and 1,3-propane sulfone was used to yield both products, respectively. A free radical copolymerization in an aqueous solution was performed to obtain PAEDAPS polymer.

Dynamic Light Scattering (DLS). The PVBT aggregate size was determined by dynamic light scattering using a goniometer system (ALV CGS-3-A0-111, Langen, Germany) equipped with a He-Ne laser (λ=632.8 nm, 22 mW) and a vertically polarized light. At an angle of 30° and temperatures ranging from 25 to 90° C., measurements were taken in 10 mm capped cylindrical borosilicate glass tubes through a reservoir filled with a refractive index matching liquid (toluene). The polymer samples of 1 mg/mL concentration were prepared in aqueous 0.1M TEABr and then filtered through a 0.1 μm Milipore filter. By pseudo-cross-correlation of the signals from two photomultipliers, the intensity autocorrelation function g (q,τ) where q=4πn$_D$ sin(θ/2)/λ was obtained with suppressed noise using ALV correlator software V.3.0. The hydrodynamic radius $R_h$ was calculated using CONTIN analysis, the distribution of $R_h$ represents the average hydrodynamic radius of all polymer molecules in solution.

$^1$H-NMR Studies. The VBT monomer (5 mg/mL) stability in $D_2O$ (with 0.5 μL DMSO as standard) and 0.5 M sodium acetate was analyzed using $^1$H-NMR (Avance-600 MHz, Bruker). The VBT peak position and integration were monitored vs. time.

Multilayer Buildup. Polyelectrolyte multilayers were built manually on double-side-polished silicon (Si 100) wafers of thickness 775 μm. The substrates were cleaned in "piranha" (70% $H_2SO_4$/30% $H_2O$), rinsed with water and dried with $N_2$. The Si wafers were dipped for 10 min in 10 mM (based on the repeat unit) polymer solutions followed by three 1 min rinses. All polymer solutions were prepared in water for TEABr concentration ranging from 0 to 2M, expect PVBT in 2M TEABr was dissolved in 1:1 water: acetone. The PAEDAPS system included polymer solutions dissolved in 0.4M NaAc.

PEMU Characterization. The thickness at every bilayer and that of the film were measured with an ellipsometer (L116S, Gartner Scientific) using a 632.8 nm laser at a 70° incidence angle. The measurement was made 4 times per sample using a PEMU refractive index of 1.55 and a 1 nm oxide layer was subtracted from the total measured value to yield the final thickness. The PEMU composition was confirmed with infrared (IR) spectroscopy using a nitrogen purged FTIR (Nicolet Avatar 360 with a DTGS detector) spectrometer. Spectra were taken averaging 100 scans at a resolution of 4 cm$^{-1}$.

Imaging. The topography of the PEMUs was obtained using a MFP-3D AFM (Asylum Research Inc., Santa Barbara, CA) with an ARC2 controller and silicon TESPA-V2 probes (Bruker, radius=10 nm, spring constant=42 N m$^{-1}$). The cantilever was adjusted to 5% below its resonance frequency and AC mode (intermittent contact) was employed. To obtain the film roughness a scan size of 1×1 μm of 1 Hz was used.

UV-Vis Turbidimetry. The solution turbidity of different complexes (1 mM) in pure water was measured by recording the absorbance at 400 nm using a UV-vis spectrophotometer (Cary 100 Bio; Varian Instruments). The normalized absorbance was plotted as a function of salt (TEABr) concentration.

Example 1. Comparisons of Polyelectrolyte Interaction Strength

The polymers selected for multilayering (Scheme 4) are a mix of commonly used positive and negative charged polymers with aromatic and aliphatic functionalities. In particular, a comparison of aliphatic tetraalkylammonium (PMAPTAC) and the aromatic thiouronium (PVBT) was made. Aliphatic tertiary ammoniums are known to form weak complexes. Concerning polyanions, aromatic sulfonates form stronger complexes than carboxylates with their positive counterparts. The polyzwitterion PAEDAPS, known to form weak (or no) complexes with polyanions and polycations, was used to evaluate the relative strength of PVBT at the highest salt concentrations.

Scheme 3. Structures of polyelectrolytes and polyzwitterion used

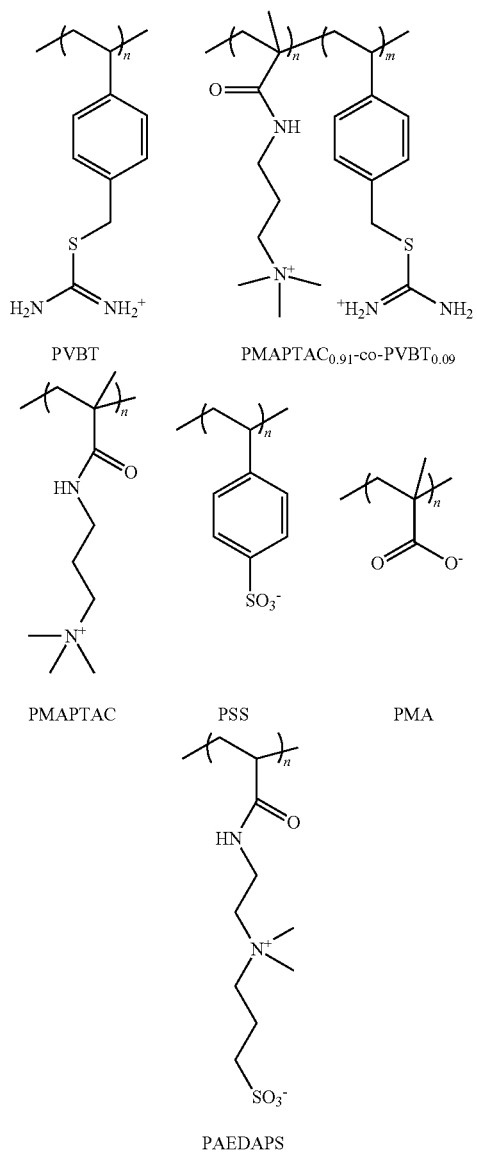

Example 2. Polythiouronium Solution Behavior

The monomer was recrystallized before use to remove any deprotected thiols. The PVBT polymer was prepared using radical polymerization in TFE and was characterized using NMR spectroscopy. Because the thiouronium group is usually employed as a precursor to thiols, via base-induced hydrolysis, the stability of the VBT monomer under neutral and mildly basic conditions was assessed by recording $^1$H-NMR spectra of VBT in $D_2O$ and in 0.5 M NaAc (pH≈9.2) for 3 weeks. The monomer showed no signs of hydrolysis in both solutions. In fact, hydrolysis is typically carried out at much higher pH.

Solutions of PVBT were difficult to prepare and work with. Hydrogen bonding interactions were believed to drive aggregation and poor solubility. Thus, while PVBT could be dispersed in water, a number of salts were found to cause precipitation, including NaCl. TEABr and sodium acetate, occupying different ends of the Hofmeister series, were found to be suitable as added salts without inducing precipitation. The size of PVBT in solution was estimated by DLS. FIGS. 1A and 1B show an autocorrelation function of solution PVBT with a single decay and a $R_h$ distribution with an average $R_h$ of 25.4 nm at 296.8 K and 339.8 K, respectively, that remains stable for at least 24 h. This $R_h$ is consistent with polymer chains in the 100s of kDa molecular weight range, or aggregates of a few smaller chains. Aggregation, indicated by large average $R_h$ and long tails to even larger $R_h$, was observed for many conditions.

Figure 2:
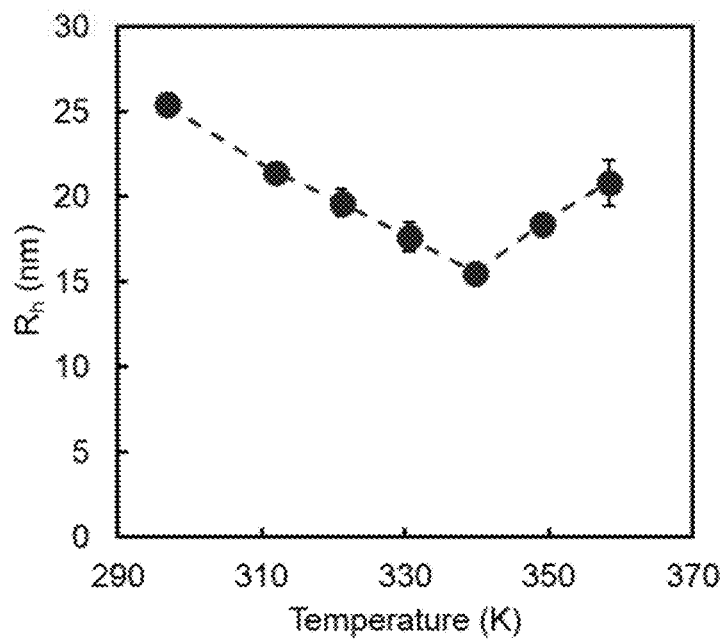
FIG. 2 shows the variation of the hydrodynamic radius $(R_h)$ of 1 mg mL$^{-1}$ PVBT in 0.1M TEABr as a function of temperature.
Figures 3A, 3B, 3C:
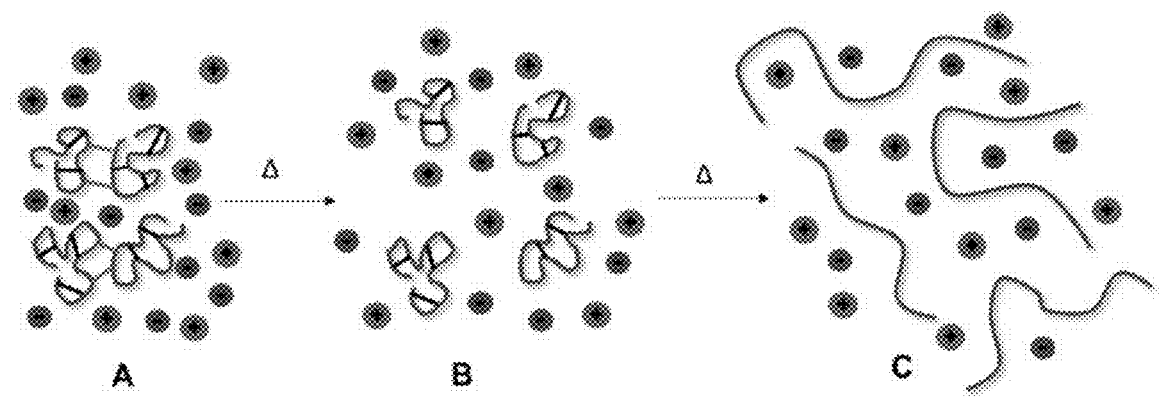
FIGS. 3A-3C show the dissociation of PVBT (red) aggregate (A) with intermolecular (grey) and intramolecular (black) H-bonds in tetraethylammonium (green) bromide (purple) solution first into individual chains with intramolecular H-bonds (B), which break on further heating (C).

The apparent size of PVBT started to decrease when heated. FIG. 2 shows first a decrease, then an increase in PVBT size with temperature, interpreted to show the breaking first of intermolecular (FIG. 3A) then intramolecular (FIG. 3B) hydrogen bonds to reach a minimum which possibly represents the size of a single polymer chain (FIGS. 1B and 3C). The $R_h$ increase at 349.1K and 358.4K (FIG. 2) can be explained by the expansion of the polyelectrolyte in solution.

Copolymers comprising at least 50 mol % MAPTAC quaternary ammonium ions were advantageously soluble in aqueous solutions, even those containing NaCl. Therefore, the ability to dissolve polymer comprising thiouronium repeat units relies on the presence of tetraalkylammonium, preferably trimethylalkyl ammonium repeat units in the copolymer.

Similarly, PVBT polymers and copolymers with MAPTAC were not soluble in ethanol, whereas the dibutyl thiouronium derivative (see below) was soluble in methanol. Therefore, the thiouronium derivatized with dibutyl is preferred for alcoholic solutions.

Example 3. Multilayer Comparisons

The differences in interaction strength between PVBT and PMAPTAC were probed using differences in layer-by-layer assembly with three polyanions. The thickness versus number of layers during PEMU growth can be either linear or nonlinear. The latter, sometimes termed "exponential" growth, is caused by mobility of one or both of the polyelectrolytes or their counterion-compensated sites. Nonlinear growth is taken as evidence of mobility within the PEMU and is generally interpreted to reflect weak interactions between positive and negative polyelectrolytes.

Figures 4A, 4B, 4C:
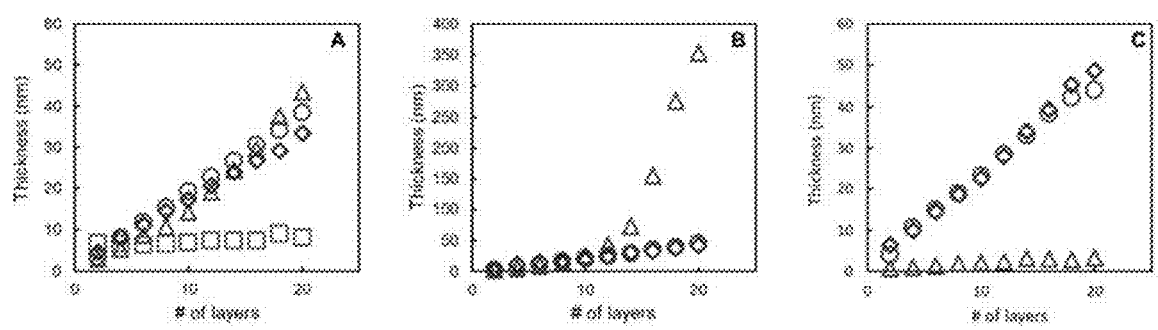
FIGS. 4A-4C show thickness vs number of layers for PEMUs made from PMAPTAC/PMA (□), PMAPTAC/PSS (Δ), PVBT/PSS (○) and PVBT/PMA (◇) constructed in (4A) 0.1M, (4B) 1M and (4C) 2M TEABr at room temperature.

FIGS. 4A-4C show the buildup of PVBT and PMAPTAC with PSS and PMA in TEABr "salt" concentrations ranging from 0.1 M to 2 M. PMAPTAC/PMA did not form a multilayer even at low salt concentrations (FIG. 4A). For PMAPTAC/PSS, at 0.1 M salt (FIG. 4A) the multilayer follows a slight nonlinear trend, it increases in thickness greatly at 1 M salt (FIG. 4B) and does not form a multilayer at all at 2 M of the organic salt (FIG. 4C). In contrast, the PVBT system keeps growing linearly, even at the highest salt concentrations (FIG. 4C) and the multilayer formed is thin and has a constant thickness. In other words, the PVBT system shows little sensitivity to salt concentration, an indication of strong interactions.

The similar behavior between the PVBT/PSS and PVBT/PMA system is somewhat surprising due to the different interaction strengths of the two polyanions in complexes. The difference between PMAPTAC and PVBT becomes more prominent at higher salt concentrations (FIGS. 4B-C). This contrasting behavior is interpreted as follows: PMAPTAC and PVBT both interact by ion pairing, which is weakened by higher salt concentration, whereas PVBT has additional attractive interactions, including hydrogen bonding.

Example 4. Interactions with Zwitterions

Figure 5:
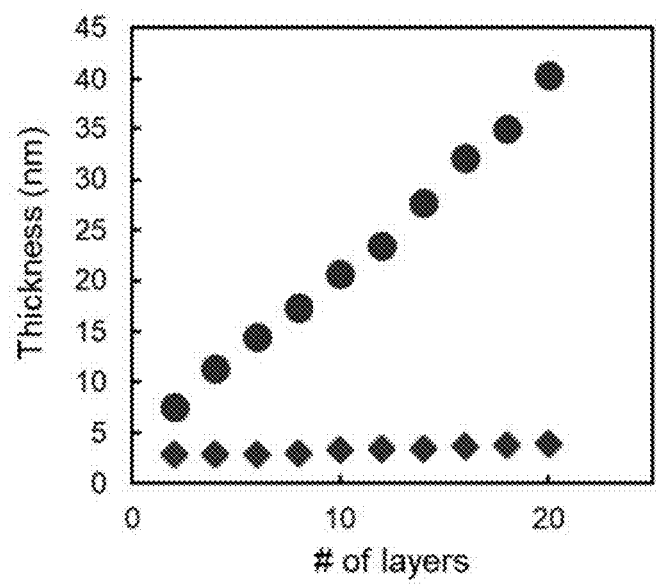
FIG. 5 shows thickness vs. number of layers for PMAPTAC/PAEDAPS (◆) and PVBT/PAEDAPS (●) PEMUs in 0.4 M NaAc at room temperature.

The exterior surface of the lipid bilayer comprises the zwitterion phosphorylcholine. The ability of the thiouronium moiety to interact with the phosphate groups prompted the use of PAEDAPS in multilayer formation. FIG. 5 depicts the linear growth of PVBT/PAEDAPS multilayer in 0.4 M NaAc whereas no PMAPTAC/PAEDAPS multilayer could be constructed under these conditions.

Example 5. Salt Resistance

Figure 6:
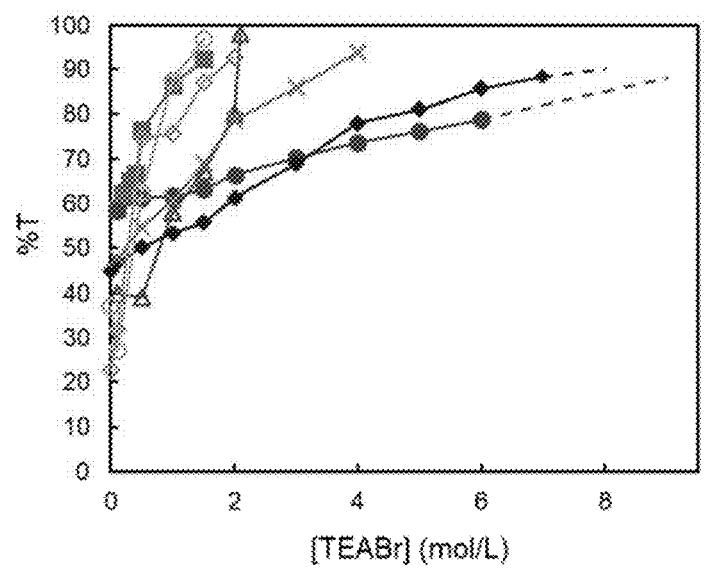
FIG. 6 shows percent transmittance of 1 mM PMAPTAC$_{0.9}$-co-PVBT$_{0.1}$/PMA (-○-), PMAPTAC$_{0.9}$-co-PVBT$_{0.1}$/PSS (-◇-), PMAPTAC/PMA (-■-), PMAPTAC/PSS (-Δ-), PVBT/PAEDAPS (-X-), PVBT/PMA (-◆-) (last data point extrapolated) and PVBT/PSS (-●-) (extrapolation to 90% T shown) solutions vs the concentration of tetraethylammonium bromide at 400 nm and room temperature.

The strength of a PEC is usually evaluated by the ability of a salt to break ion pairs. Turbidimetry is used to determine the salt concentration needed to form a homogeneous polycation and polyanion solution. FIG. 6 represents the salt resistance of various polyelectrolyte complexes. The stronger the complex, the higher the salt resistance. Thus, the polyelectrolyte complexes can be arranged from weak (PMAPTAC/PSS) to strong (PVBT/PSS) (Table 3).

Table 3 summarizes the estimated TEABr concentration needed to solubilize different PECs. This concentration was recorded at 90% transmission. A copolymer with 10% VBT was synthesized to demonstrate the effect of a small fraction of thiouronium comonomer on complexation. PMAPTAC/PMA is the weakest complex, where 1.5 M TEABr was needed to break the ion pairs. When 10% thiouronium functionality was introduced to the PMAPTAC backbone, the salt resistance of PMAPTAC/PMA increased, attaining almost the same salt concentration as that of PMAPTAC (homopolymer)/PSS. Using a strong polyanion, PSS, the salt resistance increased to 3 M with the positively charged copolymer. The strength of the PVBT interaction becomes clearer when 4 M of salt is needed to break the interactions with the weakly negative zwitterionic PAEDAPS. PSS is known to form stronger bonds than PMA thus a higher concentration of salt is needed to break the PVBT/PSS bond.

TABLE 3

Tetraethylammonium bromide (TEABr) concentration at ≥90% transmittance of different complexes

| Complex Name | $[TEABr]_{\geq 90\% T}$ (M) |
|---|---|
| PMAPTAC/PMA | 1.5 |
| PMAPTAC$_{0.9}$-co-PVBT$_{0.1}$/PMA | 2 |
| PMAPTAC/PSS | 2.1 |
| PMAPTAC$_{0.9}$-co-PVBT$_{0.1}$/PSS | 3 |
| PVBT/PAEDAPS | 4 |
| PVBT/PMA | 8-8.5 |
| PVBT/PSS | 9-9.5 |

Scheme 4. Representation of "salt-bridge" like interaction with acetate.

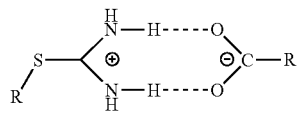

Figure 7:
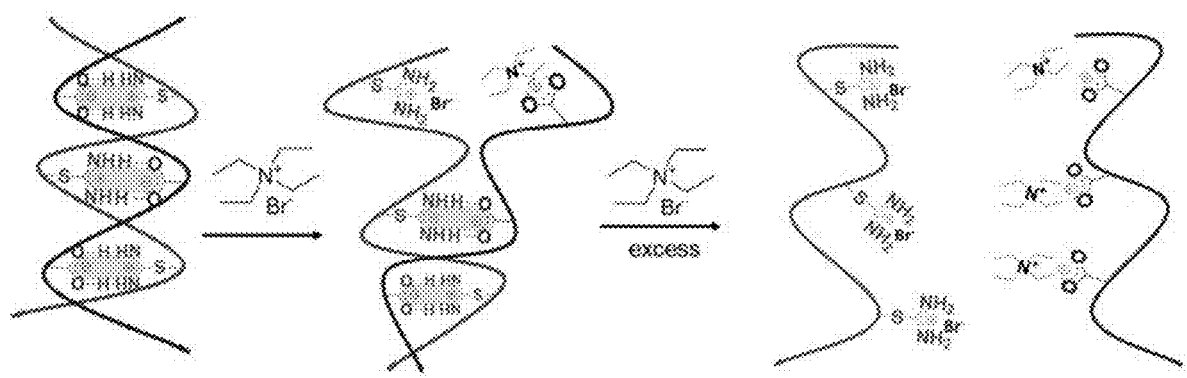
FIG. 7 shows salt resistance between PVBT (in red) and PMA (in blue). Salt must break both "electrostatic" as well as H-bonding interactions.

This high salt concentration is explained by the "salt-bridge" interaction, the carboxylate and the sulfonate are strong hydrogen bond acceptors and thus forms two types of bonds with the thiouronium; electrostatic and hydrogen bonds (Scheme 4). The tetraethylammonium and the bromide weakly interact and thus are able to disrupt the interchain polymer bonds and fully interact with the extended polymer chains (FIG. 7).

Example 6. Synthesis of Dibutyl Thiouronium Monomer

Scheme 5. Synthetic scheme of dibutyl thiouronium monomer

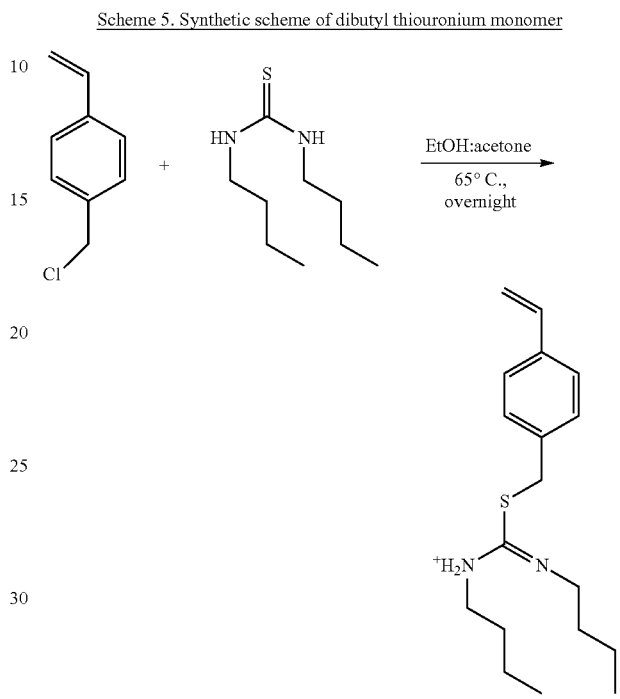

19 mmol of p-chloromethyl styrene was dissolved in 22.9 mL ethanol and 22.9 mL acetone to which 15.9 mmol of N,N-dibutylthiourea were added. The solution was left to stir under reflux for 24 h. The solvent was removed using rotary evaporator (80% yield). 1H NMR (600 MHz, DMSO-d6) δ 9.88 (d, J=5.8 Hz, 1H), 9.70 (d, J=5.7 Hz, 1H), 7.52-7.33 (m, 4H), 6.71 (dd, J=17.6, 10.9 Hz, 1H), 5.83 (d, J=17.6 Hz, 1H), 5.26 (d, J=10.9 Hz, 1H), 4.71 (s, 2H), 3.44 (d, J=7.0 Hz, 2H), 3.40-3.26 (m, 4H), 1.42 (dp, J=30.0, 7.4 Hz, 4H), 1.17 (h, J=7.4 Hz, 4H), 1.05 (t, J=7.0 Hz, 3H), 0.81 (t, J=7.3 Hz, 6H).

Example 7. Synthesis of Dibutylthiouronium Polymer

Scheme 6. Synthetic scheme of dibutyl thiouronium polymer

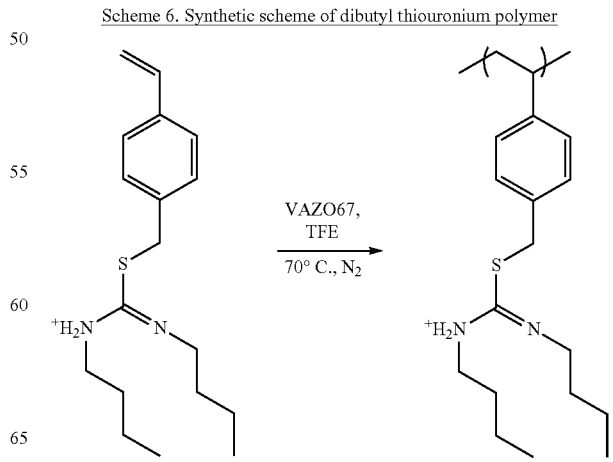

17.3 mmol of DiBuVBT in 85 mL TFE was polymerized using (34.3 mg, 1%) VAZO 67. The solution was purged with nitrogen and left to stir at 70° C. for 24 h. The solution was cooled down and the crude polymer was precipitated out using 160 mL diethyl ether and dried under vacuum at 70° C. The polymer was reprecipitated using a 1:2 ethanol: diethylether (80% yield). 1H NMR (600 MHz, Methanol-d4) δ 6.80 (dd, J=439.6, 103.0 Hz, 4H), 4.67 (s, 2H), 3.47 (s, 3H), 1.68 (s, 2H), 1.58 (s, 2H), 1.38 (s, 5H), 0.95 (d, J=14.9 Hz, 6H).

Example 8. Synthesis of Dibutylthiouronium Copolymer

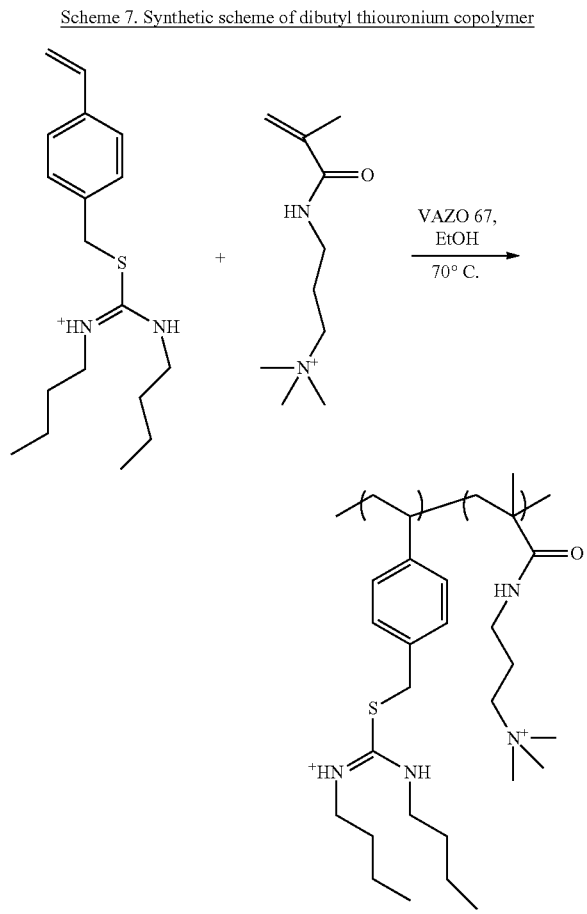

Scheme 7. Synthetic scheme of dibutyl thiouronium copolymer

MAPTAC (9.3 mmol) and DiBuVBT monomer (0.29 g, 0.99 mmol) were mixed with 38.5 mg (1.95%) VAZO 67 in 20 mL ethanol and stirred at 70° C. under $N_2$. The copolymer was purified by dialyzing against water for 48 h and recovered by evaporating the water at 70° C. under reduced pressure (70% yield). The composition was found to be PMAPTAC0.92-co-PDiBuVBT0.08. 1H NMR (600 MHz, Deuterium Oxide) δ 7.20 (dd, J=102.4, 59.1 Hz, 4H), 4.33 (s, 2H), 3.32 (s, 24H), 3.10 (s, 116H), 2.30 (s, 4H), 1.97 (s, 26H), 1.59 (d, J=106.6 Hz, 21H), 1.21 (d, J=36.2 Hz, 9H), 0.95 (d, J=106.9 Hz, 31H), 0.61 (s, 6H).

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The invention claimed is:

1. An antimicrobial copolymer comprising
   (i) a polymer backbone and a plurality of thiouronium groups covalently bonded to the polymer backbone, wherein the thiouronium group has the structure

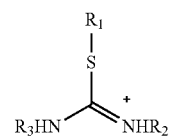

wherein $R_1$ is an aryl group, an alkylene group, or an aralkyl group that is covalently bonded to the polymer backbone, and $R_2$ and $R_3$ are independently hydrogen, an alkyl group, or an aryl group; and
   (ii) a plurality of quaternary ammonium groups covalently bonded to the polymer backbone, wherein the quaternary ammonium group has the structure

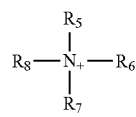

wherein $R_5$ is an aryl group or an alkylene group and is covalently bonded to the polymer backbone, and $R_6$, $R_7$, and $R_8$ are independently an alkyl group or an aryl group;
wherein the copolymer comprises the polymerization product between a first olefinic monomer having a thiouronium group and a second olefinic monomer having a quaternary ammonium group; and
wherein each thiouronium group and quaternary ammonium group has a counteranion.

2. The copolymer of claim 1, wherein $R_1$ is $C_1$ to $C_8$ alkylene group.

3. The copolymer of claim 1, wherein $R_1$ is a substituted or unsubstituted benzyl group.

4. The copolymer of claim 1, wherein the thiouronium group comprises the structure

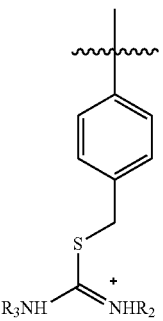

5. The copolymer of claim 1, wherein $R_2$ and $R_3$ are each a $C_2$ to $C_6$ alkyl group.

6. The copolymer of claim 1, wherein the quaternary ammonium group comprises a nitrogen-bearing heteroaryl group, wherein nitrogen alkylated.

7. The copolymer of claim 1, wherein the quaternary ammonium group comprises a nitrogen-bearing cycloalkyl group, wherein nitrogen is alkylated.

8. The copolymer of claim 1, wherein the quaternary ammonium group has the structure

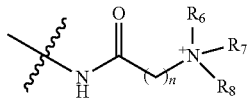

wherein n is an integer from 1 to 6.

9. The copolymer of claim 1, wherein $R_6$, $R_7$ and $R_8$ are each a $C_1$ to $C_5$ alkyl group.

10. The copolymer of claim 1, wherein $R_6$, $R_7$ and $R_8$ are each a methyl group.

11. The copolymer of claim 1, wherein the copolymer comprises a plurality of zwitterionic groups covalently bonded to the polymer backbone.

12. The copolymer of claim 1, wherein the counteranion is a halide, sulfate, or a carboxylate.

13. A composition for disinfecting a substrate comprising the copolymer of claim 1.

14. The composition of claim 13, wherein the copolymer is from about 0.001 weight percent to about 0.1 weight percent of the composition.

15. The composition of claim 13, wherein the composition comprises a solvent comprising water, an alcohol, or a combination thereof.

16. The composition of claim 13, wherein the solvent comprises at least 50 weight percent ethanol, isopropanol, or a combination thereof.

17. A method for disinfecting a substrate comprising applying to the substrate the composition of claim 13.

* * * * *